(12) United States Patent
Kadambi

(10) Patent No.: US 12,064,338 B2
(45) Date of Patent: Aug. 20, 2024

(54) IMPLANTABLE ACCOMMODATING INTRAOCULAR LENSES AND RELATED METHODS

(71) Applicant: Desikan Raiguru Kadambi, Edmonton (CA)

(72) Inventor: Desikan Raiguru Kadambi, Edmonton (CA)

( * ) Notice: Subject to any disclaimer, the term of this patent is extended or adjusted under 35 U.S.C. 154(b) by 0 days.

(21) Appl. No.: 17/024,659

(22) Filed: Sep. 17, 2020

(65) Prior Publication Data
US 2022/0079745 A1 Mar. 17, 2022

(51) Int. Cl.
*A61F 2/16* (2006.01)

(52) U.S. Cl.
CPC .......... *A61F 2/1624* (2013.01); *A61F 2/1637* (2013.01); *A61F 2002/1682* (2015.04); *A61F 2002/1683* (2013.01); *A61F 2002/1689* (2013.01)

(58) Field of Classification Search
CPC .............. A61F 2002/1683; A61F 2002/1686
See application file for complete search history.

(56) References Cited

U.S. PATENT DOCUMENTS

| | | | |
|---|---|---|---|
| 4,159,546 A | 7/1979 | Shearing | |
| 4,173,798 A | 11/1979 | Welsh | |
| 4,174,543 A * | 11/1979 | Kelman | A61F 2/1605 623/6.43 |
| 4,244,060 A | 1/1981 | Hoffer | |
| 4,249,271 A | 2/1981 | Poler | |
| 4,270,230 A | 6/1981 | Poler | |
| 4,315,337 A * | 2/1982 | Choyce | A61F 2/1602 623/6.43 |
| 4,424,597 A | 1/1984 | Schlegel | |
| 4,446,582 A | 5/1984 | Hanna | |
| 4,787,902 A * | 11/1988 | Sheets | A61F 2/16 623/6.51 |
| 4,842,601 A | 6/1989 | Smith | |
| 4,878,912 A | 11/1989 | Castleman | |
| 4,888,012 A | 12/1989 | Horn | |

(Continued)

FOREIGN PATENT DOCUMENTS

| | | |
|---|---|---|
| CA | 2212459 | 5/2006 |
| FR | 2794965 | 12/2000 |

(Continued)

OTHER PUBLICATIONS

Mayo Clinic, screenshots taken from YouTube video Intraocular Lenses, available at least as early as May 9, 2011, 3 pages, URL = https://www.youtube.com/watch?v=9QS1YpwZVjQ.

(Continued)

*Primary Examiner* — Leslie A Lopez
(74) *Attorney, Agent, or Firm* — Robert A. Nissen

(57) ABSTRACT

An implantable accommodating intraocular lens (IOL) has an optic lens sized to fit within a capsular lens bag of an eye; and a plurality of haptics angularly spaced around and radially extended from the optic lens, with each haptic: having a tongue that forms an arcuate sulcus gripping part that, in use within the capsular lens bag, inserts into and follows a circumferential groove of the sulcus to restrict circumferential sliding of the tongue around the sulcus; and being structured to move, under contraction and expansion of ciliary muscles of the eye, to adjust the optic lens to accommodate a focal power of the eye.

13 Claims, 3 Drawing Sheets

(56) References Cited

U.S. PATENT DOCUMENTS

| | | | |
|---|---|---|---|
| 5,019,099 A | | 5/1991 | Nordan |
| 5,489,302 A | * | 2/1996 | Skottun ................ A61F 2/1694 623/6.13 |
| 5,928,282 A | * | 7/1999 | Nigam ................ A61F 2/1613 623/6.43 |
| 5,984,962 A | | 11/1999 | Anello |
| 6,176,878 B1 | | 1/2001 | Gwon |
| 6,302,911 B1 | | 10/2001 | Hanna |
| 6,461,384 B1 | | 10/2002 | Hoffman |
| 6,749,633 B1 | | 6/2004 | Lorenzo |
| 7,018,410 B1 | | 3/2006 | Vazeen |
| 7,118,597 B2 | | 10/2006 | Miller |
| 8,579,971 B2 | | 11/2013 | Webb |
| 2003/0130733 A1 | | 7/2003 | Paul |
| 2003/0187505 A1 | | 10/2003 | Liao |
| 2004/0249456 A1 | | 12/2004 | Cumming |
| 2005/0119741 A1 | | 6/2005 | Cumming |
| 2006/0100704 A1 | * | 5/2006 | Blake ................ A61F 2/15 623/6.37 |
| 2010/0070030 A1 | * | 3/2010 | Amon ................ A61F 2/1602 623/6.49 |
| 2010/0106245 A1 | | 4/2010 | Rombach |
| 2012/0046744 A1 | | 2/2012 | Woods |
| 2014/0336757 A1 | | 11/2014 | Simonov |
| 2016/0143728 A1 | | 5/2016 | De Smet |
| 2016/0331520 A1 | * | 11/2016 | Beer ................ A61F 2/1629 |
| 2019/0254809 A1 | | 8/2019 | Dworschak |

FOREIGN PATENT DOCUMENTS

| | | |
|---|---|---|
| JP | 2005161075 | 1/2005 |
| MX | 2011005583 | 10/2011 |
| WO | 2000066040 | 11/2000 |
| WO | 2007081311 | 7/2007 |
| WO | 2015044235 | 4/2015 |

OTHER PUBLICATIONS

Douglas Grayson, The Ins and Outs of Lens Explantation, Oct. 4, 2011, Review of Opthalmology, 6 pages, URL = https://www.reviewofophthalmology.com/article/the-ins-and-outs-of-lens-explantation.

Sonia Kelley, Accommodating Intraocular Lenses (IOL) for Cataract Surgery, Available at least as early as Feb. 2019, 6 pages, URL= https://www.allaboutvision.com/conditions/accommodating-iols.htm.

Medhelp, comments and replies in Eye Care Communities board, Available at least as early as Dec. 10, 2007, 14 pages, URL = https://www.medhelp.org/posts/Eye-Care/Many-problems-with-Crystalens/show/374063.

Enette Ngoei, The pros and cons of multifocal and accommodating IOLs, available at least as early as Feb. 2008, 4 pages, URL = https://www.eyeworld.org/article-the-pros-and-cons-of-multifocal-and-accomodating-iols.

Einstein Medical, Crystalens, Available at least as early as Sep. 6, 2017, 5 pages, URL = https://www.docshop.com/education/vision/refractive/iol/crystalens.

Reviews Talk, Consumer reviews of CRYSTALENS, Available at least as early as Jan. 25, 2012, 9 pages, URL = https://www.reviewstalk.com/complaints-reviews/crystalens-I9810.html.

Complaint Board, Consumer complaints and reviews about CRYSTALENS, available as early as Jan. 1, 2016, 5 pages, URL = https://www.complaintboard.com/crystalens-I317.html.

Health Boards Health Message Boards, Crystalens problems message board, available as early as Oct. 2007, 8 pages, URL = https://www.healthboards.com/boards/eye-vision/539837-crystalens-problems.html.

Machine Translation of JP2006034917, published Feb. 9, 2006, URL: https://worldwide.espacenet.com/patent/search/family/035900516/publication/JP2006034917A?q=pn%3DJP2006034917A, 7 pages.

Eyesmart—American Academy of Opthalmology, screenshots taken from YouTube video Intraocular Lenses (IOLs) and Cataract Surgery, available at least as early as Jul. 29, 2016, 4 pages, URL = https://www.youtube.com/watch?v=Ui9ylzckiDg.

Google, screenshot of Google image search results for "Intraocular lens", available at least as early as Apr. 3, 2020, 1 page.

Machine Translation of DE10125829, published Nov. 28, 2002, URL: https://worldwide.espacenet.com/patent/search/family/007686330/publication/DE10125829A1?q=pn%3DDE10125829A1, 3 pages.

* cited by examiner

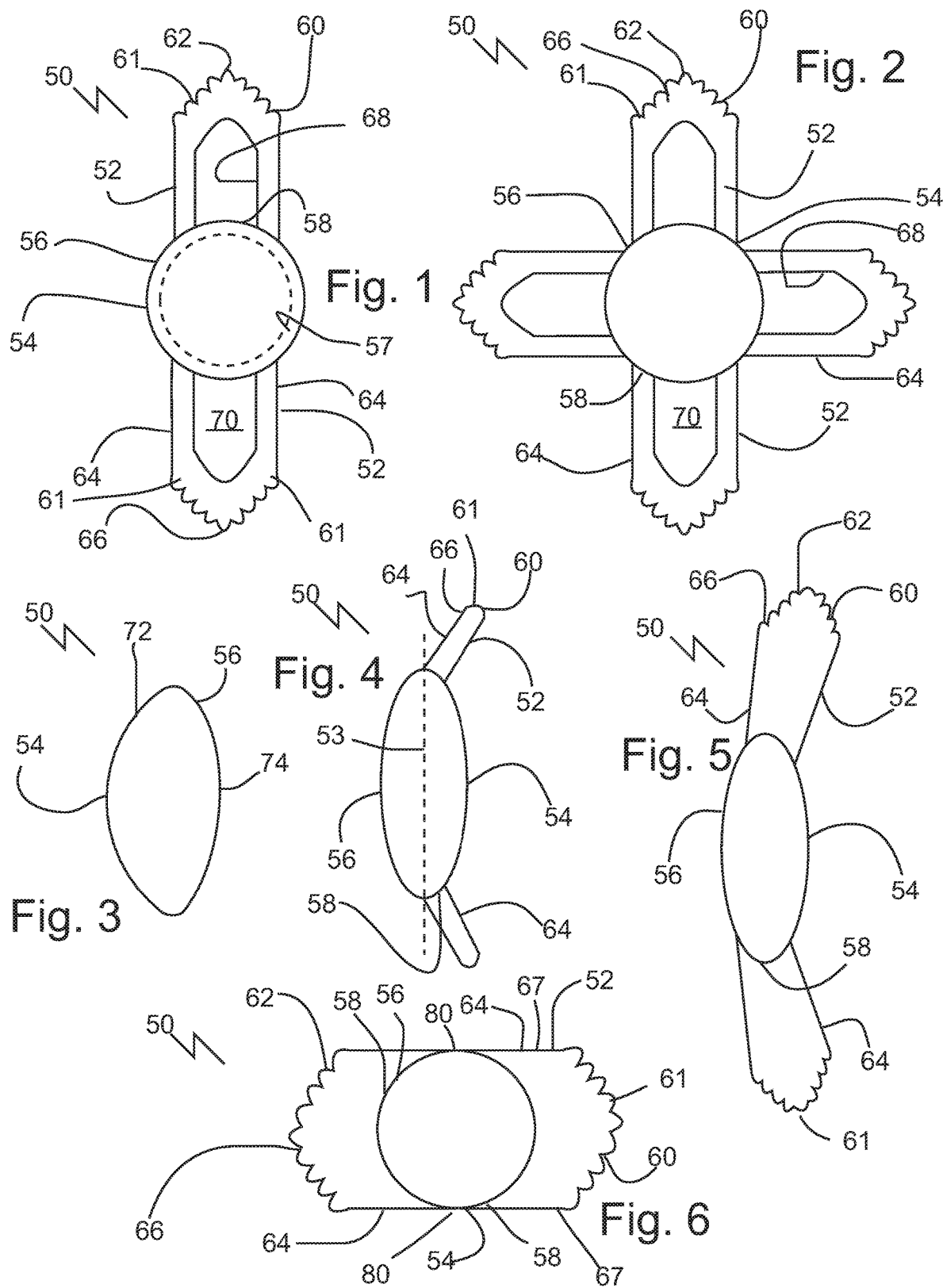

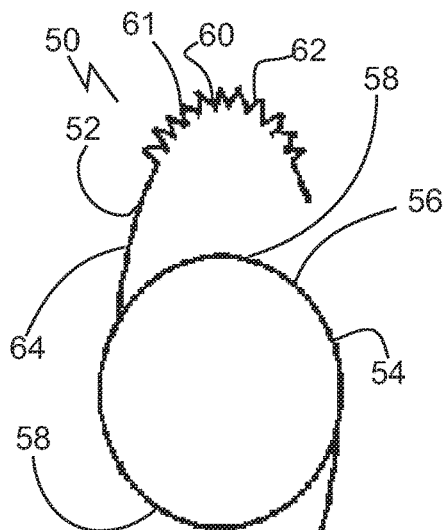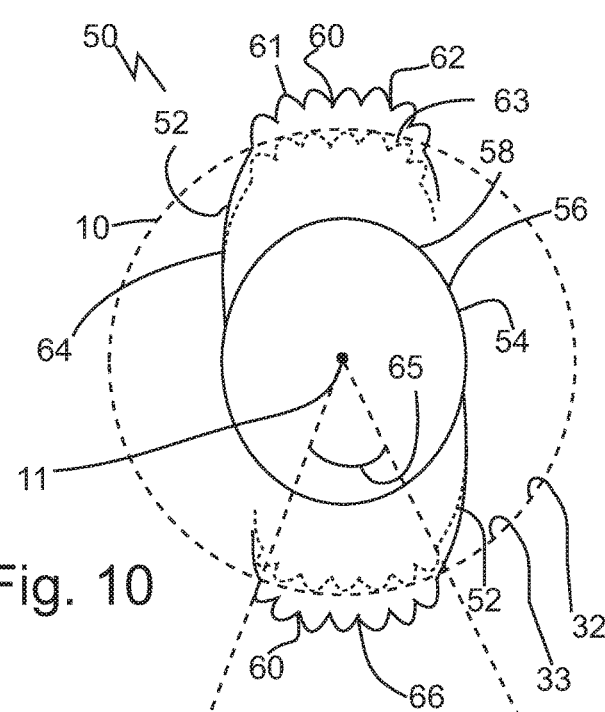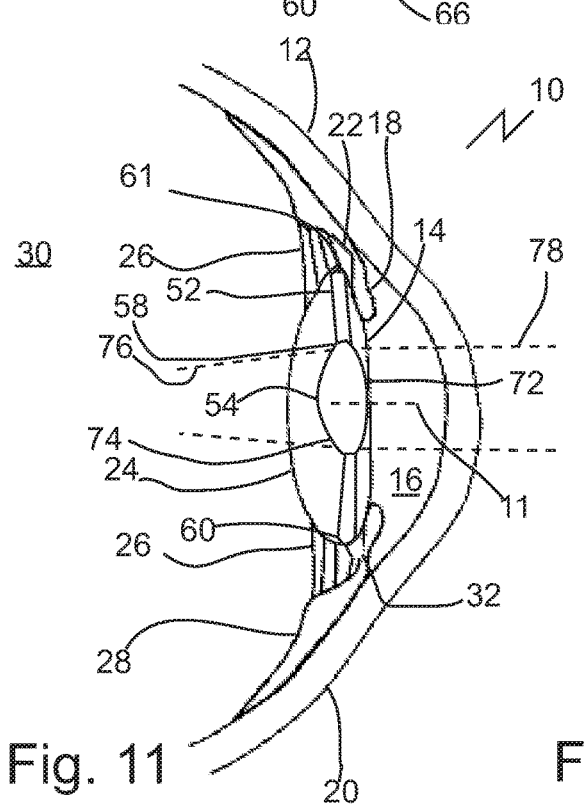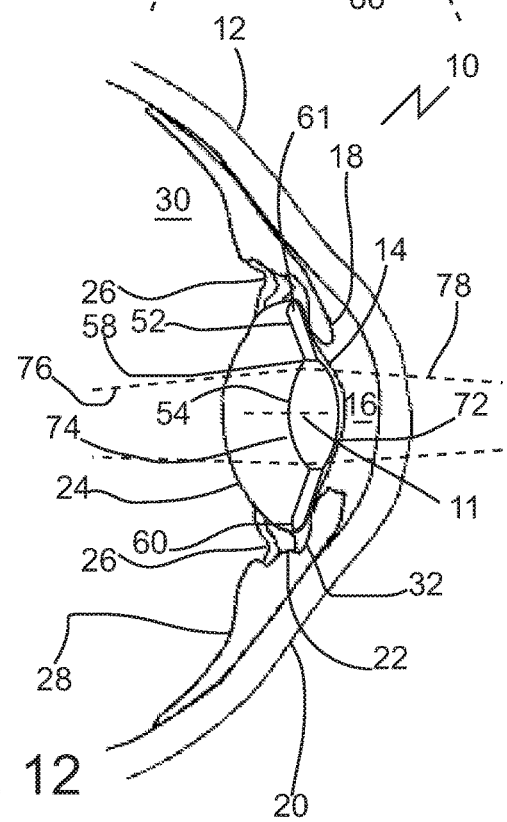

IMPLANTABLE ACCOMMODATING INTRAOCULAR LENSES AND RELATED METHODS

TECHNICAL FIELD

This document relates to implantable accommodating intraocular lenses and related methods.

BACKGROUND

The following paragraphs are not an admission that anything discussed in them is prior art or part of the knowledge of persons skilled in the art.

Multifocal or monofocal intraocular lenses (IOLs) may be inserted in the capsular lens bag of the eye to provide improved vision at a variety or a single focal distance. Accommodating lenses such as the Crystalens™ fit within the capsular lens bag via haptics.

SUMMARY

An implantable accommodating intraocular lens (IOL) is disclosed comprising: an optic lens sized to fit within a capsular lens bag of an eye; and a plurality of haptics angularly spaced around and radially extended from the optic lens, with each haptic: having a tongue that forms an arcuate sulcus gripping part that, in use within the capsular lens bag, inserts into and follows a circumferential groove of the sulcus to restrict circumferential sliding of the tongue around the sulcus; and being structured to move, under contraction and expansion of ciliary muscles of the eye, to adjust the optic lens to accommodate a focal power of the eye.

A combination is disclosed comprising an implantable accommodating IOL fitted within a capsular lens bag of an eye, with respective arcuate sulcus gripping parts of the plurality of haptics inserted into and following the circumferential groove of the sulcus of the eye.

A method is also disclosed comprising inserting an implantable accommodating IOL into a capsular lens bag of an eye.

A method is disclosed comprising inserting an implantable accommodating IOL into a capsular lens bag of an eye, through an incision in the capsular lens bag, such that the arcuate sulcus gripping parts of the plurality of haptics insert into and follow the circumferential groove of the sulcus to grip the sulcus.

A method is disclosed comprising: inserting an implantable accommodating intraocular lens (IOL) into a capsular lens bag of an eye, through an incision in an anterior portion of the capsular lens bag, to position the implantable accommodating IOL such that: arcuate sulcus gripping parts of a plurality of haptics are inserted into and follow a circumferential groove of the sulcus to grip the sulcus; and under contraction and expansion of ciliary muscles of the eye, the plurality of haptics move to adjust the optic lens to accommodate a focal power of the eye.

In various embodiments, there may be included any one or more of the following features: The arcuate sulcus gripping part is formed on an outer radially-facing edge of the tongue. The arcuate sulcus gripping part forms a circular arc. Each arcuate sulcus gripping part forms an arc subtending an angle of between 20 and 95 degrees about an optical axis defined by the optic lens. In which the arcuate sulcus gripping part comprises a plurality of protrusions on a surface of the tongue. The plurality of protrusions are convex. The plurality of protrusions are shaped in a wave pattern. The wave pattern is an absolute value sinusoidal wave. Each haptic has an arm with a first end that originates at the optic lens and a second end that defines the tongue. Each haptic comprises a pair of arms angularly spaced from one another, with the arcuate sulcus gripping part bridging the second ends of the pair of arms. The plurality of haptics comprises a pair of haptics that are opposed to one another and whose lateral edges extend tangentially from respective opposed poles of a circumferential edge of the optic lens. Each haptic is mounted posteriorly to the optic lens. Each haptic is mounted to move the optic lens anteriorly and posteriorly, under contraction and relaxation, respectively, of the ciliary muscles of the eye. The plurality of haptics are structured with sufficient radial extension such that, in use, the plurality of haptics are under radial compression by the ciliary muscles when the ciliary muscles are in a relaxed state. The plurality of haptics comprises two to eight haptics. The optic lens defines an opaque circumferential edge region to reduce night glare. Inserting further comprises inserting the implantable accommodating IOL in a folded configuration into the capsular lens bag. Prior to inserting, destroying a natural crystalline lens of the eye. Prior to inserting, forming the incision.

The foregoing summary is not intended to summarize each potential embodiment or every aspect of the subject matter of the present disclosure. These and other aspects of the device and method are set out in the claims.

BRIEF DESCRIPTION OF THE FIGURES

Embodiments will now be described with reference to the figures, in which like reference characters denote like elements, by way of example, and in which:

FIG. 1 is a front elevation view of an implantable accommodating intraocular lens (IOL), having an optic lens and two opposed haptic arms with a plurality of convex protrusions along respective arcuate sulcus gripping parts.

FIG. 2 is a front elevation view of an implantable accommodating IOL, having an optic lens and four haptic arms with a plurality of convex protrusions along respective arcuate sulcus gripping parts.

FIG. 3 is a side elevation view of the optic lens of FIGS. 1 and 2.

FIG. 4 is a side elevation view of the implantable accommodating IOL of FIG. 1.

FIG. 5 is a perspective side view of implantable accommodating IOL of FIG. 4.

FIG. 6 is a front elevation view of an embodiment of an implantable accommodating IOL, having an optic lens and two wide haptic arms with a plurality of convex protrusions along respective arcuate sulcus gripping parts.

FIG. 9 is a front elevation view of an embodiment of an implantable accommodating IOL, having an optic lens and two arcuate haptic arms with a plurality of protrusions along respective arcuate sulcus gripping parts.

FIG. 10 is a front elevation view of an embodiment of an implantable accommodating IOL, having an optic lens and two arcuate haptic arms with a plurality of convex protrusions along arcuate sulcus gripping parts, with the movement of the haptics during accommodation shown in dashed lines, and with the location of the circumferential groove of the sulcus shown in dashed lines.

FIG. 11. is a cross-sectional side view of an embodiment of the implantable accommodating IOL of FIG. 1 positioned in a human eye after the removal of the natural crystalline lens, in which the ciliary muscles are shown relaxed, with the lens zonules taut, such that the lens is accommodating for far-sighted viewing of a distant focal point, with focal lines of light illustrated with dashed lines and travelling from the focal point and through the lens.

FIG. 12. is a cross-sectional side view of the implantable accommodating IOL and eye combination of FIG. 11 in which the ciliary muscles are contracted and the lens zonules are slacked, such that the lens is accommodating for near-sighted viewing of a nearby focal point (relative to the focal point in FIG. 11), with focal lines of light illustrated with dashed lines and travelling from the focal point and through the lens. In FIG. 12 the lens is moved forward relative to the position the lens adopts in FIG. 11.

DETAILED DESCRIPTION

Figure 7:
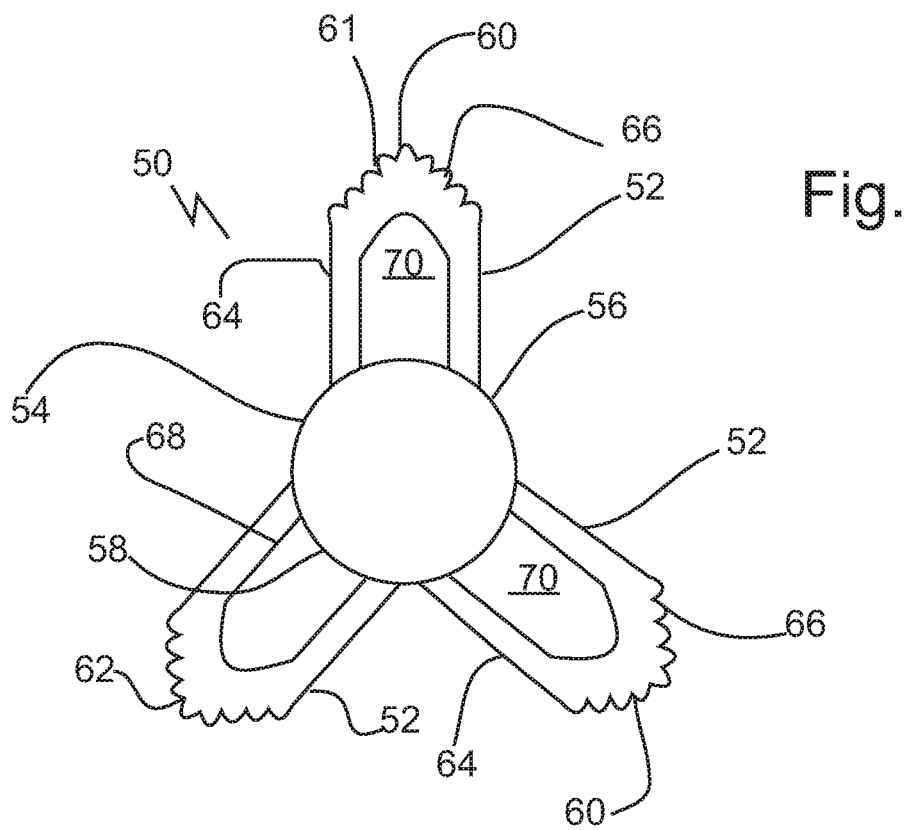
FIG. 7 is a front elevation view of an embodiment of an implantable accommodating IOL, having an optic lens and three haptic arms with a plurality of convex protrusions along respective arcuate sulcus gripping parts.

Immaterial modifications may be made to the embodiments described here without departing from what is covered by the claims.

Problems with vision may take numerous forms. These include myopia (nearsightedness), hyperopia (farsightedness) as well as cataracts (opacification of the lens). Contact lenses and glasses containing refractive lenses are commonly used for basic correction of myopia, hyperopia, and astigmatism. Both contact lenses and glasses represent non-permanent solutions that are susceptible to loss, breakage and require cleaning in order to maintain efficacy.

An implantable intraocular contact lens, known as an IOL, is a surgical implantation used to permanently improve an eyesight condition, such as myopia, hyperopia or cataracts. An IOL incorporates a corrective lens tailored and structured to the degree of vision impairment desired to be corrected. An IOL solution may be a viable option for a patient who has a condition that would otherwise disqualify them from alternative laser-assisted in situ keratomileusis (LASIK) treatment such as: thin corneas, dry eyes or astigmatism (imperfection in the curvature of the lens). An IOL may be considered and used as a permanent vision correction solution, but may be removed or adjusted to address any change in efficacy or in a patient's vision deficit.

Two types of IOL solutions exists—phakic and pseudophakic. With a phakic solution ('phakic' meaning "having a lens") the eye's natural lens is left untouched. Intraocular lenses that are implanted into eyes after the eye's natural lens has been removed during cataract surgery are known as pseudophakic. Phakic intraocular lenses are indicated for patients with high refractive errors when the usual laser options for surgical correction (LASIK and PRK) are contraindicated. Phakic IOLs may be designed to correct high myopia ranging from −5 to −20 D if the patient has enough anterior chamber depth (ACD) of at least 3 mm. The most common type of IOL is the pseudophakic IOL, which may be implanted after the eye's natural lens has been removed. The pseudophakic IOL provides the same light focusing function as the natural crystalline lens. A pseudophakic IOL may be available as: monofocal (focus on only one distance), multifocal (for example bifocal), or accommodating (permits focus changing).

An IOL may contain non-optic side struts known as haptics. A haptic may be the part of an IOL responsible for its attachment to the ciliary muscles or suspensory ligaments called lens zonules, which are connected to both the ciliary muscle and natural crystalline lens within the capsular lens bag of the eye. Haptics may use hinges at its ends to aid in attaching to the ciliary muscles or zonules. In any given IOL, the haptics may vary in number and shape, including having loops or hooks, for example having loops to sew into the ciliary sulcus of the eye.

Accommodation is how an eye may change optical power to maintain a clear image as the eye focuses on objects at different distances. When the eye focuses on an object that is relatively far away, the ciliary muscles may relax, leading to the lens zonules becoming taut, leading to a flattening of the natural crystalline lens. When the eye focuses on an object that is relatively near an individual, the ciliary muscles may contract, leading to the lens zonules slackening, reducing tension upon the natural crystalline lens, making the lens more convex.

An IOL may be designed to use non-optical elements known as haptics to connect to the ciliary muscles or zonules of the eye, allowing for accommodation to occur. With an accommodating IOL, the accommodation process may occur as a result of one or more of a change in the shape of the lens or a change in the position of the lens relative to the lens capsule. In the case of the former (change in lens shape causing accommodation), similar to the natural crystalline lens, when viewing an object that is relatively nearby, the ciliary muscles may contract, resulting in reduced tension on the haptics, resulting in the lens becoming convex in shape. As well, when viewing an object that is relatively far away, the ciliary muscles relax, increasing the tension on the haptics and flattening the natural crystalline lens. In the case of the latter (movement of lens causing accommodation), accommodation may occur through the haptics changing the position of the lens anterior or posterior relative to the lens capsule. When viewing an object that is relatively nearby, for example a book held at arm's length, under the tension of the contracted ciliary muscles the haptics may push the lens in an anterior direction, moving the lens relatively closer to the pupil. When viewing an object that is far away, the ciliary muscles may relax, resulting in the haptics pushing the lens in a posterior direction, moving the lens relatively further from the pupil. It is through such anterior-posterior movement of the lens that accommodation may be achieved in a manner analogous to that of the natural eye.

In contrast to accommodation, a static or non-accommodating IOL may be used, for example with a monofocal or multifocal lens. A monofocal lens may only focus at a single distance, for example a distance over 20 meters to correct only distance vision. A multifocal IOL may have plural regions that each focus at different relative distances, for example two or three focal regions spaced throughout the lens simultaneously based on the position of the pupil. In some cases, the central part of the lens may be designed for focusing on nearby objects, while the outer regions of the lens may be structured for focusing on far away objects. When viewing a nearby object, the pupil of the eye may constrict and the central region of the IOL may be used, while for far away viewing the pupil dilates and an outer IOL focal region may be used.

Some newer lens designs attempt to allow the eye to regain some partial focusing ability in order to change focus from distance to near via accommodation. However, many accommodating IOLs used today only achieve a very limited improvements in near vision which reduced over time.

Accommodative IOLs may also have a slightly higher risk of developing posterior capsule opacification (PCO), though there is some uncertainty around this finding. PCO is a common side-effect of many cataract surgeries and is easily treatable with a one-time laser capsulotomy procedure. Accommodating IOLs interact with ciliary muscles and zonules, using hinges at both ends to latch on and move forward and backward inside the eye using the same mechanism as normal accommodation. The haptic hinges may be made of an advanced silicone called BioSil that has been thoroughly tested to make sure it is capable of unlimited flexing in the eye.

An IOL may be implanted in a surgical procedure. A surgeon may use drugs to dilate the pupil of the patient. A cut may be made into the cornea and anterior capsular lens bag of the eye, where the natural crystalline lens is contained, to facilitate the insertion of surgical tools and an IOL. The natural crystalline lens may be destroyed in what is known as a pseudophakic procedure, by a suitable technique such as the use of a laser or ultrasound. In some cases, it may be unnecessary to destroy the crystalline lens, such as where the crystalline lens has already been removed or destroyed in a previous procedure, as might be the case where an IOL is being replaced or upgraded. Alternatively, in a phakic procedure the natural crystalline lens may be kept intact. An IOL may then be inserted into the capsular lens bag. Insertion may be achieved by folding the IOL and inserting it through the cut made in the anterior lens capsule lens, assuming that the IOL is made with flexible material. The non-optic haptics may contact the sulcus of the eye.

There may be various problems with IOLs. Stiff haptics may impair the ability of the ciliary muscles to change the shape of the lens. Stiff haptics may further make it difficult to remove an IOL if a patient elects to do so after having a phakic procedure. Lens zonules may drive accommodation as opposed to the ciliary muscles, reducing the eye's ability to accommodate as following the initial cut into the anterior lens capsule the zonular system may not perform as efficiently as pre-surgery to change the shape of the lens. IOLs may need to be tailored in size to a patient's eye, and thus would not be considered to be one-size-fits-all. As the sulcus shape to which the IOL must match cannot be accurately measured, a surgeon may implant either too large of an optic lens, which will resist ciliary muscle action, or too small of an optic lens, in which the ciliary muscle may not accommodate properly or at all.

Referring to FIGS. 1-2 and 4-12, an implantable accommodating intraocular lens (IOL) 50 has an optic lens 54 and a plurality of haptics 52. Optic lens 54 may be sized to fit the capsular lens bag of an eye 10. Haptics 52 may be angularly spaced around and radially extended from the optic lens 54. Referring to FIG. 4, the haptics 52 may be attached posteriorly to the optic lens 54, for example posterior of a central plane 53 defined through the lateral sides of the lens 54. Posterior attachment may assist the implantable accommodating IOL 50 to move forward during ciliary muscle contraction, and may assist with implantation by facilitating the ability of the IOL 50 to assume a compact, folded state for implantation. Referring to FIGS. 3-5, an optic lens 54 may have a flat posterior 74 and a rounded anterior 72, or another suitable shape. Referring to FIGS. 11 and 12, during implantation, the implantable accommodating IOL 50 may be inserted into the capsular lens bag of an eye 10 with or without the removal of the natural crystalline lens in what is known as a pseudophakic or phakic surgical procedure, respectively. Each haptic 52 may be structured to move, under contraction and expansion of ciliary muscles of the eye 10, to adjust one or more of a position or shape of the optic lens to accommodate a focal power of the eye 10.

Referring to FIGS. 1-2 and 4-10, the haptics 52 may have suitable characteristics. The implantable accommodating IOL 50 may have a haptic 52 with an arm 64 that defines a first, anchor end 58, for example that originates at the optic lens 54, and a second, sulcus end 61 that may define the tongue 60. The anchor end 58 of the haptic 52 may be directly attached to the optic lens 54. The sulcus end 61 may form the arcuate sulcus gripping part 66 to aid in attachment to the sulcus 32 of the eye 10.

Figure 8:
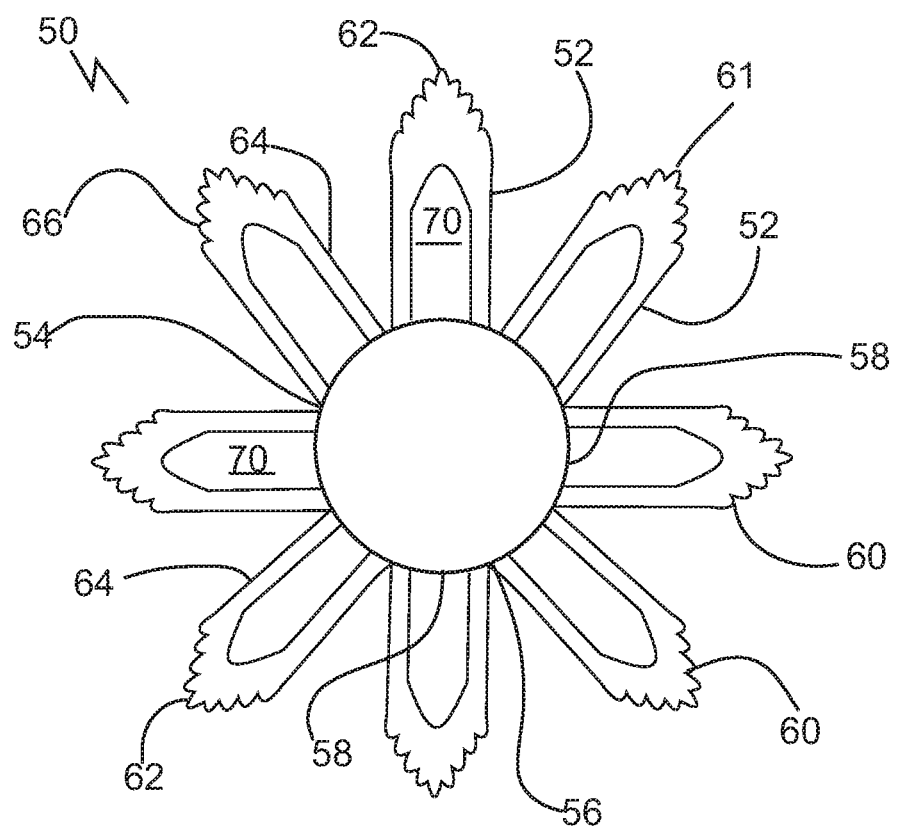
FIG. 8 is a front elevation view of an embodiment of an implantable accommodating IOL, having an optic lens and eight haptic arms with a plurality of convex protrusions along respective arcuate sulcus gripping parts.

Referring to FIGS. 1-2 and 7-10, an implantable accommodating IOL 50 may have a suitable number and arrangement of haptics 52. For example, in FIG. 2, the embodiment has two haptics 52, opposed from one another. In FIG. 8 the IOL 50 has eight haptics 52. A relatively increased number of haptics 52 may help distribute the force of the ciliary muscles 28 evenly across the optic lens 54, thereby leading to more effective accommodation of the IOL 50 as opposed to only two haptics 52. Other examples in the figures show three and four haptics (FIGS. 7 and 2, respectively), although any suitable number of haptics may be used. In some cases, the implantable accommodating IOL 50 may have between two and eight haptics.

Referring to FIGS. 10-12, each haptic 52 may have a tongue 60 that forms an arcuate sulcus gripping part 66. In use within the capsular lens bag 24, the gripping part 66 may insert into and follow a circumferential groove 33 (FIG. 10) of the sulcus 32 to restrict circumferential sliding of the tongue 60 around the sulcus 32. A plurality of haptics 52 may contain tongues 60 that insert into and follow the circumferential groove 33 (FIG. 10) of the sulcus 32 of the eye 10. The use of sulcus gripping parts may prevent rotation of the lens 54 about an optical axis 11 of the eye 10. An optical axis 11 may be defined as a line that passes through a center of the eye 10 and a center of the pupil. In use, the implantable accommodating IOL 50 may be fitted within a capsular lens bag 24 of an eye 10, with the respective tongues 60 of the plurality of haptics 52 inserted into and following the circumferential groove 33 of the sulcus 32 of the eye 10.

Referring to FIGS. 10-12, the arcuate sulcus gripping part 66 of the implantable accommodating IOL 50 may be contained within the capsular lens bag 24, and inserts into and follows the circumferential groove 33 of the sulcus 32 to restrict circumferential sliding of the tongue 60 around the sulcus 32. A gripping effect may be achieved via friction created between the circumferential groove 33 of the sulcus 32 and the arcuate sulcus gripping part 66 through the capsular lens bag 24 wall, by sandwiching the bag 24 between the gripping part 66 and the sulcus 32. Referring to FIG. 5, the arcuate sulcus gripping part 66 may be formed on an outer radially facing edge 63 of the tongue 60. Placing the arcuate sulcus gripping part 66 along the outer radically facing edge 63 of the tongue 60 may help the gripping part 66 to better follow the natural curve of the sulcus 32 of the eye 10, and therefore may assist movement of the implantable accommodating IOL 50 after it has been surgically inserted. Referring to FIG. 10, the arcuate sulcus gripping part 66 may form a circular arc which subtends an angle 65, for example between 20 and 95 degrees about the optical axis 11 defined by the optical lens 54.

Referring to FIGS. 1-2 and 5-10, the arcuate sulcus gripping part 66 may be formed by a plurality of protrusions 62 on the surface of the tongue 60. The plurality of protrusions may comprise a series of protrusions 62 arrayed along an outer radial-facing edge 63 of the arcuate sulcus gripping part 66. Referring to FIG. 9 the protrusions 62 may have a suitable shape, for example a repeating prong structure to engage the surface of the sulcus 32 through the bag 24. Each prong may be pointed, for example by rising at 45 degrees to meet a pointed peak. Referring to FIG. 10, the protrusions 62 may have a wavy or curved shape. Referring to FIGS. 11 and 12, protrusions may increase the surface area available on the implantable accommodating IOL 50 to grip to the sulcus 32, and therefore may better conduct the movement of the ciliary muscles 28 and lens zonules 26 to the haptics 52, which in turn may act to change the shape of the optic lens 54 during accommodation.

Referring to FIGS. 1-2, 5-8 and 10, the plurality of protrusions 62 may have a wavy shape. In some cases, the protrusions are convex. A convex shape may be a shape with an outer profile that extends outward from the lens 54 and is curved, for example along a circular, elliptical, or parabolic line. The convex protrusions may meet at respective bases, forming a concave transition between adjacent protrusions. The plurality of protrusions 62 may be shaped in a wave pattern. In some cases, the wave pattern is an absolute value sine wave (with the understanding that this is equivalent to an absolute value cosine wave given the lack of a definable x-axis). Pointed, curved, or other convex protrusions along the sulcus gripping edge 63 may increase the surface area available on the implantable accommodating IOL 50 to grip the sulcus 32 of the eye 10.

Referring to FIG. 11, the plurality of haptics 52 may be structured with sufficient radial extension such that, in use the plurality of haptics 52 are under radial compression by the ciliary muscles 28 when the ciliary muscles 28 are in a relaxed state. Such an effect may be achieved by using long travel haptics 52, and/or haptics sized to a larger diameter of radial extension than the sulcus 32 into which the IOL 50 is implanted. By providing a neutral-state compression of the optic lens 54 achieved by haptics 52 from the initial implantation, the IOL 50 may better remain in the correct position relative to the optical axis 11, improving the function of the IOL 50.

Referring to FIGS. 11 and 12, each haptic 52 may be mounted to move the optic lens 54 anteriorly and posteriorly, under contraction and relaxation, respectively, of the ciliary muscles 28 of the eye 10, to achieve accommodation. Referring to FIG. 11, in the neutral state of the eye 10, the ciliary muscles 28 may be relaxed and the lens zonules 26, which are suspensory ligaments attached on opposing side to both the ciliary muscles 28 and the capsular lens bag 24, are taut presenting a stretched appearance. This movement of the ciliary muscles 28 and the lens zonules 26 in turn stretches the capsular lens bag 24 and enlarges the sulcus 32, allowing the natural resiliency of the haptics 52 to press into the sulcus 32 and cause the optic lens 54 to move posteriorly relative to the capsular lens bag 24. Light from a distant image is able to travel from an object, through the lens 54, and to a focal point at the optic nerve 76, presenting a clear image. Referring to FIG. 12, if an object is relatively close to the eye 10, the ciliary muscles 28 may contract, reducing the tension in the lens zonules 26 and causing them to slack. The slacking of the lens zonules 26 may reduce the diameter of the sulcus 32, forcing the haptics 52 to push the optic lens 54 anteriorly towards the pupil 14. Light is then able to travel from the object to the lens 54, and to a focal point at the optic nerve 76, presenting a clear image. It is through the movement of the lens 54 that an implantable accommodating IOL 50 may act analogous to how the natural crystalline lens would when viewing objects at different distances.

Referring to FIGS. 11 and 12, in some cases the haptic 52 is mounted to change the shape of the optic lens 54, under contraction and relaxation of the ciliary muscles 28 of the eye 10, to achieve accommodation. Referring to FIG. 11, in the neutral state of the eye 10, the ciliary muscles 28 may be relaxed and the lens zonules 26 may be taut presenting a stretched appearance. This movement of the ciliary muscles 28 and the lens zonules 26 in turn stretches the capsular lens bag 24 and enlarges the diameter of the sulcus 32, allowing the natural resiliency of the haptics 52 to press into the sulcus 32 and cause the optic lens 54 to relax and elongate. Light from a distant image is able to travel from an object, through the lens 54, and to a focal point at the optic nerve 76, presenting a clear image. Referring to FIG. 12, if an object is relatively close to the eye 10, the ciliary muscles 28 may contract, reducing the tension in the lens zonules 26 and causing them to slack. The slacking of the lens zonules 26 may reduce the diameter of the sulcus 32, forcing the haptics 52 to push against and compress the optic lens 54, bulging or rounding the lens anteriorly. Light is then able to travel from the object to the lens 54, and to a focal point at the optic nerve 76, presenting a clear image. It is through the distortion or change of shape of the lens 54 that an implantable accommodating IOL 50 may act analogous to how the natural crystalline lens would when viewing objects at different distances. In some cases, the IOL 50 is structured to both move and change shape to achieve accommodation.

Referring to FIGS. 1-2 and 7-8, the haptics 52 may have a suitable structure, such as a bridged structure shown. Referring to FIG. 1, each haptic 52 may comprise a pair of arms 64 angularly spaced from another, with the arcuate sulcus gripping part 66 bridging the second ends 61 of the pair of arms 64. This embodiment creates a haptic 52 in which there is a cutout or gap 70 between the pair of haptic arms 64. The cutout or gap 70 between the pair of arms may be defined by the inner edge of the haptic 68. Gaps 70 may be used or tailored to improve or adjust the flexibility of the haptic 52.

Referring to FIG. 6, the haptics 52 may have a bulged appearance. In this example the IOL 50 has a pair of haptics 52 that are opposed to one another and whose lateral edges 67 extend tangentially from respective opposed poles 80 at the anchor end 58 of the haptic 52 from of a circumferential edge 56 of the optic lens 54. As above, the arcuate sulcus gripping parts 66 may have a suitable shape, such as a plurality of protrusions 62 that are convex in shape and arranged in a wave pattern.

Referring to FIG. 1, the implantable accommodating IOL 50 may be structured for glare reduction or removal. The optic lens 54 may define an opaque circumferential edge region 57, for example extending up to and radially inward from circumferential edge 56. In the example shown, the opaque region 57 is denoted by the ring-shaped area contained between the circle in dashed lines and the circumferential edge 56. Having an opaque region may help to reduce night glare, which is the difficulty of seeing in the presence of bright lights, for example car headlamps, during the night. In some cases, colored or patterned material may be used to reduce night glare. In some cases, material may be used to cause total internal reflection about the edge region to reduce or eliminate glare.

Referring to FIGS. 11 and 12, the implantable accommodating IOL 50 may implanted via a suitable method, which may include making an incision in the eye 10. Prior to inserting the implantable accommodating IOL 50, an incision may be formed into the cornea 12 and anterior chamber 16 of the eye 10. This method may not need to be performed if a patient has a pre-existing incision in the anterior chamber 16, for example if they previously had phakic or pseudophakic surgery and were simply replacing the implantable accommodation IOL 50. A surgeon may use a suitable tool to make the incision, for example lasers. The anterior chamber 16 incision may be used for the insertion of the implantable accommodating IOL 50.

Referring to FIGS. 11 and 12, a suitable implantation method may incorporate the destruction or removal of the natural crystalline lens of the eye 10. Such a method may be performed in a pseudophakic surgery, such as for the removal of a cataract, where the natural crystalline lens of the eye 10 must be destroyed and/or removed. In a phakic surgery the natural crystalline lens may be retained in the capsular lens bag 24 of the patient with the implantable accommodating IOL 50 surgically inserted on top of the natural crystalline lens. The natural crystalline lens of the eye 10 may be destroyed using a suitable technique, such as using ultrasound waves through phacoemulsification. The process of phacoemulsification may use an ultrasonic probe to break up and emulsify the natural crystalline lens into liquid using the energy of ultrasound waves. The resulting emulsion may be vacuumed out through the use of surgical tools. Alternatively, a laser may be used to soften the natural crystalline lens as it is broken up before phacoemulsification is performed to remove it. Using lasers to soften followed by ultrasound to break up may help to ensure there are no sharp-edged debris formed as a result of the destruction of the natural lens, as such debris could otherwise cause damage to the eye 10 during the removal of the natural lens from the capsular lens 24.

Referring to FIGS. 11 and 12, an implantation method may involve inserting the IOL 50 into the capsular lens bag of an eye 10 via a suitable method. Insertion may be carried out through the incision made prior in an anterior chamber 16 of the capsular lens bag 24 of an eye 10, such that the arcuate sulcus gripping parts 66 of the plurality of haptics 52 insert into and follow the circumferential groove 33 of the sulcus 32. The IOL 50 may be inserted in a compact, such as a folded, configuration, into the capsular lens bag 24, which may be advantageous to retain the IOL 50 in the bag 24 and also to reduce the size of incision required.

In the claims, the word "comprising" is used in its inclusive sense and does not exclude other elements being present. The indefinite articles "a" and "an" before a claim feature do not exclude more than one of the feature being present. Each one of the individual features described here may be used in one or more embodiments and is not, by virtue only of being described here, to be construed as essential to all embodiments as defined by the claims.

The embodiments of the invention in which an exclusive property or privilege is claimed are defined as follows:

1. An implantable accommodating intraocular lens (IOL) comprising:
    an optic lens sized to fit within a capsular lens bag of an eye;
    a plurality of haptics angularly spaced around and radially extended from the optic lens, with each haptic:
        having an arm with a first end that originates at the optic lens and a second end that defines a tongue that forms an arcuate sulcus gripping part that, in use within the capsular lens bag, inserts into and follows a circumferential groove of a sulcus to restrict circumferential sliding of the tongue around the sulcus, in which the arcuate sulcus gripping part comprises a plurality of protrusions spaced in a circumferential direction along the tongue, in which a maximum width of the arm, defined in a plane perpendicular to an optical axis of the optic lens, is equal to or smaller than a diameter of the optic lens;
        being attached posteriorly to the optic lens, at an attachment point that is closer to a posterior than to an anterior of the optic lens to move the entire optic lens anteriorly and posteriorly, along the optic axis of the eye, under contraction and relaxation, respectively, of ciliary muscles of the eye, to adjust the optic lens to accommodate a focal power of the eye; and
        being structured to prevent rotation of the optic lens about an optical axis of the eye in use; and
    in which the implantable accommodating IOL is structured to assume a compact, folded state for implantation; and
    in which the plurality of haptics are structured with sufficient radial extension such that, in use, the plurality of haptics are under radial compression by the ciliary muscles when the ciliary muscles are in a relaxed state.

2. The implantable accommodating IOL of claim 1 in which the arcuate sulcus gripping part is formed on an outer radially-facing edge of the tongue.

3. The implantable accommodating IOL of claim 2 in which the arcuate sulcus gripping part forms a circular arc.

4. The implantable accommodating IOL of claim 1 in which each arcuate sulcus gripping part forms an arc subtending an angle of between 20 and 95 degrees about the optical axis defined by the optic lens.

5. The implantable accommodating IOL of claim 4 in which the plurality of protrusions are shaped in a wave pattern.

6. The implantable accommodating IOL of claim 5 in which the wave pattern is an absolute value sinusoidal wave.

7. The implantable accommodating IOL of claim 1 in which the plurality of protrusions are convex.

8. The implantable accommodating IOL of claim 1 in which, for each haptic, the arm comprises a pair of arms angularly spaced from one another, with the arcuate sulcus gripping part bridging the second ends of the pair of arms.

9. The implantable accommodating IOL of claim 1 in which the plurality of haptics comprises two to eight haptics.

10. The implantable accommodating IOL of claim 1 in which the optic lens defines an opaque circumferential edge region to reduce night glare.

11. A combination comprising the implantable accommodating IOL of claim 1 fitted within the capsular lens bag of the eye, with the respective arcuate sulcus gripping parts of the plurality of haptics inserted into and following the circumferential groove of the sulcus of the eye.

12. An implantable accommodating intraocular lens (IOL) comprising:
    an optic lens sized to fit within a capsular lens bag of an eye;
    a plurality of haptics angularly spaced around and radially extended from the optic lens, with each haptic:
        having an arm with a first end that originates at the optic lens and a second end that defines a tongue that forms an arcuate sulcus gripping part that, in use within the capsular lens bag, inserts into and follows a circumferential groove of a sulcus to restrict circumferential sliding of the tongue around the sulcus, in which the arcuate sulcus gripping part comprises a plurality of protrusions spaced in a circumferential direction along the tongue, in which a maximum width of the arm, defined in a plane perpendicular to an optical axis of the optic lens, is equal to or smaller than a diameter of the optic lens;

being attached posteriorly to the optic lens, at an attachment point that is closer to a posterior than to an anterior of the optic lens to move the entire optic lens anteriorly and posteriorly, along the optic axis of the eye, under contraction and relaxation, respectively, of ciliary muscles of the eye, to adjust the optic lens to accommodate a focal power of the eye; and being structured to prevent rotation of the optic lens about an optical axis of the eye in use; and in which the implantable accommodating IOL is structured to assume a compact, folded state for implantation; and in which:

each arcuate sulcus gripping part forms an arc subtending an angle of between 20 and 95 degrees about the optical axis defined by the optic lens;

the plurality of protrusions are shaped in a wave pattern; and the wave pattern is an absolute value sinusoidal wave.

13. An implantable accommodating intraocular lens (IOL) comprising:

an optic lens sized to fit within a capsular lens bag of an eye;

a plurality of haptics angularly spaced around and radially extended from the optic lens, with each haptic:

having an arm with a first end that originates at the optic lens and a second end that defines a tongue that forms an arcuate sulcus gripping part that, in use within the capsular lens bag, inserts into and follows a circumferential groove of a sulcus to restrict circumferential sliding of the tongue around the sulcus, in which the arcuate sulcus gripping part comprises a plurality of protrusions spaced in a circumferential direction along the tongue, in which a maximum width of the arm, defined in a plane perpendicular to an optical axis of the optic lens, is equal to or smaller than a diameter of the optic lens;

being attached posteriorly to the optic lens, at an attachment point that is closer to a posterior than to an anterior of the optic lens to move the entire optic lens anteriorly and posteriorly, along the optic axis of the eye, under contraction and relaxation, respectively, of ciliary muscles of the eye, to adjust the optic lens to accommodate a focal power of the eye; and being structured to prevent rotation of the optic lens about an optical axis of the eye in use; and in which the implantable accommodating IOL is structured to assume a compact, folded state for implantation; and in which, for each haptic, the arm comprises a pair of arms angularly spaced from one another, with the arcuate sulcus gripping part bridging the second ends of the pair of arms.

* * * * *